US009125844B1

(12) United States Patent
Morrison et al.

(10) Patent No.: US 9,125,844 B1
(45) Date of Patent: *Sep. 8, 2015

(54) NUTRITIONAL SUPPLEMENTS FOR WOMEN DESIRING TO BECOME PREGNANT, AND PREGNANT AND NURSING WOMEN

(75) Inventors: John C. Morrison, Jackson, MS (US); Kenneth R. Greathouse, Los Altos, CA (US)

(73) Assignee: Argent Development Group, LLC, Mountain View, CA (US)

( * ) Notice: Subject to any disclaimer, the term of this patent is extended or adjusted under 35 U.S.C. 154(b) by 1089 days.

This patent is subject to a terminal disclaimer.

(21) Appl. No.: 12/379,487

(22) Filed: Feb. 24, 2009

Related U.S. Application Data

(63) Continuation-in-part of application No. 12/232,551, filed on Sep. 19, 2008, now Pat. No. 7,964,189.

(60) Provisional application No. 61/128,823, filed on May 27, 2008, provisional application No. 60/995,065, filed on Sep. 25, 2007.

(51) Int. Cl.
*A61K 38/00* (2006.01)

(52) U.S. Cl.
CPC ..................................... *A61K 38/00* (2013.01)

(58) Field of Classification Search
CPC ... A61K 2300/00; A61K 33/24; A61K 33/06; A61K 33/04; A61K 31/198; A61K 33/30; A61K 45/06; A61K 31/385; A61K 33/26; A61K 33/34; A61K 31/375; A61K 31/202; A61K 31/185; A61K 31/20; A61K 31/355; A61K 33/32
See application file for complete search history.

(56) References Cited

U.S. PATENT DOCUMENTS

| | | | |
|---|---|---|---|
| 4,599,152 A | 7/1986 | Ashmead | |
| 4,814,177 A | 3/1989 | Walsdorf et al. | |
| 4,822,816 A | 4/1989 | Markham | |
| 4,830,716 A | 5/1989 | Ashmead | |
| 4,968,716 A | 11/1990 | Markham | |
| 5,070,085 A | 12/1991 | Markham | |
| 5,407,957 A | 4/1995 | Kyle et al. | |
| 5,492,938 A | 2/1996 | Kyle et al. | |
| 5,494,678 A | 2/1996 | Paradissis et al. | |
| 5,494,681 A | 2/1996 | Cuca et al. | |
| 5,516,925 A | 5/1996 | Pedersen et al. | |
| 5,869,084 A | 2/1999 | Paradissis et al. | |
| 5,895,652 A | 4/1999 | Giampapa | |
| 5,945,123 A | 8/1999 | Hermelin | |
| 5,948,443 A | 9/1999 | Riley et al. | |
| 5,976,568 A | 11/1999 | Riley et al. | |
| 6,197,329 B1 | 3/2001 | Hermelin et al. | |
| 6,214,379 B1 | 4/2001 | Hermelin | |
| 6,228,388 B1 | 5/2001 | Paradissis et al. | |
| 6,258,846 B1 | 7/2001 | Hermelin et al. | |
| 6,261,600 B1 | 7/2001 | Kirschner et al. | |
| 6,299,896 B1 | 10/2001 | Cooper et al. | |
| 6,352,713 B1 | 3/2002 | Kirschner et al. | |
| 6,361,800 B1 | 3/2002 | Cooper et al. | |
| 6,479,545 B1 | 11/2002 | Levinson et al. | |
| 6,488,956 B1 | 12/2002 | Paradissis et al. | |
| 6,569,857 B1 | 5/2003 | Hermelin et al. | |
| 6,576,666 B2 | 6/2003 | Hermelin et al. | |
| 6,660,293 B2 | 12/2003 | Giordano et al. | |
| 6,696,083 B1 | 2/2004 | Paradissis et al. | |
| 6,716,814 B2 | 4/2004 | Ericson et al. | |
| 6,814,983 B2 | 11/2004 | Giordano et al. | |
| 6,818,228 B1 | 11/2004 | Walsdorf et al. | |
| 6,863,904 B2 | 3/2005 | Giordano et al. | |
| 6,914,073 B2 | 7/2005 | Boulos et al. | |
| 6,953,588 B2 | 10/2005 | Cooper et al. | |
| 7,022,350 B2 | 4/2006 | Harvey et al. | |
| 7,112,609 B2 | 9/2006 | Hermelin et al. | |
| 7,205,007 B2 | 4/2007 | Lane | |
| 7,238,373 B2 | 7/2007 | Meyrowitz | |
| 7,390,509 B2 | 6/2008 | Giordano et al. | |
| 2004/0001817 A1 | 1/2004 | Giampapa | |
| 2004/0248183 A1* | 12/2004 | Argyropoulos et al. | 435/6 |
| 2005/0037065 A1 | 2/2005 | Kirschner et al. | |
| 2005/0101670 A1 | 5/2005 | Hermelin et al. | |
| 2005/0106266 A1 | 5/2005 | Levinson et al. | |
| 2006/0115556 A1* | 6/2006 | Foulger et al. | 426/72 |
| 2006/0121129 A1 | 6/2006 | Harvey et al. | |
| 2006/0134227 A1 | 6/2006 | Bortz et al. | |
| 2007/0231312 A1* | 10/2007 | Muench et al. | 424/94.1 |
| 2008/0152725 A1* | 6/2008 | Giordano et al. | 424/638 |

OTHER PUBLICATIONS

Baby Hopes Supplement Data Sheet.
Citra Natal DHA, CitraNatal 90 DHA, and Citra Natal Rx Product Data Sheet.
Citracal Prenatal + DHA Product Data Sheet.
Citracal Prenatal 90+DHA Product Data Sheet.
Centrum Materna Product Data Sheet.
PreCare Premier Product Data Sheet.
PrimaCare Product Data Sheet.
PreCare Chewables Product Data Sheet.
PreCare Conceive Product Data Sheet.
PrimaCare One Product Data Sheet.
Long's Complete Premium Women's High Potency Multivitamin/Multimineral Supplement with Herbs—two sides of external package.

* cited by examiner

*Primary Examiner* — Debbie K Ware
(74) *Attorney, Agent, or Firm* — Joseph I. Hirsch

(57) ABSTRACT

The disclosure relates to nutritional supplements to be administered to, or to be taken by, women desiring to become pregnant, and pregnant and nursing women, so that a woman (and any fetus) will be nutritionally supplemented before, during and after the gestation period. The nutritional supplements have a blend of folic acid, lycopene and co-enzyme QIO, optionally docosahexaenoic acid, and other vitamins and minerals, and a nutritionally acceptable carrier therefor, but are free or substantially free of other materials in nutritionally effective amounts. Specific nutritional supplements are described.

57 Claims, No Drawings

NUTRITIONAL SUPPLEMENTS FOR WOMEN DESIRING TO BECOME PREGNANT, AND PREGNANT AND NURSING WOMEN

CROSS REFERENCE TO RELATED APPLICATIONS

This application claims priority from U.S. Provisional Application Ser. No. 60/995,065, filed Sep. 25, 2007 and U.S. Provisional Application Ser. No. 61/128,823, filed May 27, 2008, and is a continuation-in-part application of utility application Ser. No. 12/232,551, filed Sep. 19, 2008, the disclosures of which are all incorporated herein by this reference.

FIELD OF THE INVENTION

The present invention relates to nutritional supplements to be administered to, or to be taken by, women desiring to become pregnant, and pregnant and nursing women.

BACKGROUND OF THE INVENTION

The present invention relates to nutritional supplements to be administered to, or to be taken by, women desiring to become pregnant, and pregnant and nursing women. It is known that there are numerous deficiencies in the diets of pregnant and nursing women, particularly, but not exclusively, women of low and moderate incomes. More broadly, diets of people in general, and women in particular, in the United States are known to be poor, due in part to the prevalence of so-called "junk food", fast food, which is high in caloric content, but low in nutritional value, and the desire of many working people to eat prepared food after a long day at the office. For women of child-bearing age, the situation becomes worse when they become pregnant and thereafter during pregnancy as what the fetus needs may not be provided by a given woman's normal daily dietary intake.

Many supplements have been proposed and are currently being marketed in the United States to overcome the nutritional deficiencies caused by such eating habits. For example, Hermelin et al. in U.S. Pat. Nos. 6,258,846, 6,576,666 and 7,112,609 describe in the Background of the Invention sections of their respective inventions, various formulations and supplements, including prenatal formulations and supplements, that are (or were) on the market in the United States and contain various combinations of ingredients to supplement the nutrition, among others, of pregnant and nursing women. These include products known by the names Materna, Enfamil Natalins RX, Prenate Ultra, Niferex-PN, Niferex-PN Forte, Advanced Formula Zenate, Precare, and Natafort, all marketed by various companies that own the trademarked names of these products.

Riley U.S. Pat. Nos. 5,948,443 and 5,976,568 and Cooper et al. U.S. Pat. Nos. 6,299,896, 6,361,800 and 6,953,588 describe multi-vitamin and mineral supplements also including amounts of lycopene and co-enzyme Q10. These supplements are described as general wellness supplements for a wide range of people, but are not specifically described as being useful for pregnant and/or nursing women.

Many of the supplements described above, and elsewhere in the literature, including those supplements currently on the market in the United States, contain a broad range of ingredients, many of which are not necessary to be administrated to pregnant or nursing women. While they may not do any harm, in the sense that the body will eliminate in one way or another that which is not needed, there is a preference, and it is our desire, to set forth unique supplement formulations that have those, and only those, ingredients that serve necessary and beneficial purposes, particularly for pregnant and nursing women, or women desiring to become pregnant.

BRIEF SUMMARY OF THE INVENTION

The unique supplements of the present invention are particularly suited for being administered to, or to be taken by, pregnant and nursing women and are free of any other added vitamins and minerals. However, they may also be administered to, or taken by, women desiring to become pregnant, so that any ensuing pregnancy (and thus the fetus) will be nutritionally supplemented from the very beginning of gestation.

The unique supplement formulations of the present invention are exemplified by the following specific embodiments.

In the broadest embodiment of the present invention, the nutritional supplement comprises a daily dose of:
- about 2,000 to about 8000 IU of Vitamin A,
- about 1 to about 5 mg of Vitamin $B_1$,
- about 1 to about 15 mg of Vitamin $B_2$,
- about 2 to about 12 mcg of Vitamin $B_{12}$,
- about 60 to 200 mg of Vitamin C,
- about 200 to about 500 IU of Vitamin $D_3$,
- about 10 to about 40 mg of Vitamin E,
- about 100 to about 500 mg of a lycopene-containing material,
- about 50 to about 200 mg of co-enzyme Q10,
- about 50 to about 250 mg of docosahexaenoic acid (DHA),
- about 50 to about 100 mg of docusate sodium,
- about 1 to 3 mg of copper,
- about 1 to about 5 mg of folic acid,
- about 30 to about 90 mg of iron,
- about 10 to about 100 mg of magnesium,
- about 10 to about 30 mcg of selenium,
- about 15 to about 30 mg of zinc, and
- a pharmaceutically or nutritionally acceptable carrier therefor.

In a preferred embodiment of the present invention, a nutritional supplement consists essentially of a daily dose of:
- about 2,500 IU (1.5 mg) of Vitamin A,
- about 2 mg of Vitamin $B_1$,
- about 10 mg of Vitamin $B_2$,
- about 2 mcg of Vitamin $B_{12}$,
- about 100 mg of Vitamin C,
- about 240 IU (6 mcg) of Vitamin $D_3$,
- about 20 mg of Vitamin E,
- about 400 mg of a 5% lycopene-containing material affording about 20 mg of actual lycopene,
- about 100 mg of co-enzyme Q10,
- about 200 mg of docosahexaenoic acid (DHA),
- about 50 mg of docusate sodium,
- about 2 mg of copper,
- about 1 mg of folic acid,
- about 60 mg of iron,
- about 30 mg of magnesium,
- about 15 mcg of selenium,
- about 25 mg of zinc, and
- a pharmaceutically or nutritionally acceptable carrier therefor.

In a particularly preferred embodiment of the present invention, a nutritional supplement consists of a daily dose of:
- about 2,500 IU of Vitamin A (as beta-carotene),
- about 2 mg of Vitamin $B_1$,
- about 3.4 mg of Vitamin $B_2$,
- about 2 mcg of Vitamin $B_{12}$,
- about 60 mg of Vitamin C, about 240 IU (6 mcg) of Vitamin $D_3$,
about 20 mg of Vitamin E,
about 200 mg of a 5% lycopene-containing material affording about 10 mg of actual lycopene,
about 100 mg of co-enzyme Q10,
about 100 mg of docosahexaenoic acid (DHA),
about 50 mg of docusate sodium,
about 2 mg of copper,
about 1 mg of folic acid,
about 30 mg of iron (preferably carbonyl iron),
about 20 mg of magnesium,
about 15 mcg of selenium,
about 25 mg of zinc, and
a pharmaceutically or nutritionally acceptable carrier therefor.

In another particularly preferred embodiment of the present invention, a nutritional supplement consists of a daily dose of:
about 2,000 IU (1.2 mg) of Vitamin A (as beta-carotene),
about 2 mg of Vitamin $B_1$,
about 3.4 mg of Vitamin $B_2$,
about 2 mcg of Vitamin $B_{12}$,
about 60 mg of Vitamin C,
about 240 IU (6 mcg) of Vitamin $D_3$,
about 10 mg of Vitamin E,
about 100 mg of a 5% lycopene-containing material affording about 5 mg of actual lycopene,
about 200 mg of co-enzyme Q10,
about 200 mg of docosahexaenoic acid (DHA),
about 100 mg of docusate sodium,
about 2 mg of copper,
about 1 mg of folic acid,
about 60 mg of iron (preferably carbonyl iron),
about 10 mg of magnesium,
about 15 mcg of selenium,
about 15 mg of zinc, and
a pharmaceutically or nutritionally acceptable carrier therefor.

A further aspect of the present invention is a nutritional supplement having folic acid, a lycopene-containing material, co-enzyme Q10 and a pharmaceutically or nutritionally acceptable carrier, wherein the supplement, is free of calcium and chromium. In a further embodiment, the supplement is free of one or more (e.g., all) of calcium, chromium, potassium, alpha-carotene, choline, lutein, zeaxanthin, and vitamin K. In a further embodiment, such a supplement is additionally free of one or more (e.g., all) of biotin, iodine, and pantothenic acid. In a further embodiment, such a supplement is additionally free of vitamin $B_3$ and herbs or herb extracts. In yet a further embodiment, such a supplement is free of calcium, chromium, iodine, manganese, molybdenum, potassium, vitamin $B_3$, vitamin $B_5$, vitamin K, herbs or herb extracts, alpha-carotene, alpha-lipoic acid, biotin, choline, lutein, omega acids other than DHA, panthothenic acid, succinic acid and zeaxanthin. The supplements of the present invention are free of other added minerals, vitamins, and nutritional ingredients or therapeutic agents (e.g., aspirin), provided, however, that they may contain other ingredients as set forth herein, particularly the ingredients set forth in Paragraph[0009] above, in the amounts set forth therein, or in the more specific amounts as set forth in Paras. [0010], [0011] and [0012].

The preferred form of administration of the supplements of the present invention is tablets, taken once daily in the amounts set forth above in the morning along with breakfast or after any early morning nausea has passed. However, smaller tablets may be used if administration is desired to be twice daily, or three times daily, for example, at other or each mealtime, or after any pregnancy-induced nausea may have subsided, so that, in the aggregate, the daily administration will be in the amounts as set forth herein.

The supplements of this invention can be packaged in unit dosage form in combination with labeling instructions for supplementing the diet of a woman desiring to become pregnant, and pregnant and nursing women. The instructions will be what is conventional in this field, namely how many of the dosage forms (preferably tablets) are to be taken daily and at what time during the day they are to be taken, plus any other instructions that might be applicable to the supplements of this invention.

DETAILED DESCRIPTION OF THE INVENTION

Vitamin A plays an important role in maintaining the integrity of all epithelial tissues (skin/mucous membrane). It is also essential in the synthesis of retinal pigmentation and deficiency leads to a variety of ophthalmic problems. This vitamin is essential for normal fetal development and conversely deficiency leads to congenital malformations as well as fetal mortalities. The present invention includes about 2,000 IU/day to about 8000 IU/day, preferably about 2,500 IU (1.5 mg)/day, of Vitamin A, as beta-carotene, to supply the developing fetus with adequate amounts of this essential vitamin regardless of maternal diet. Each IU of beta-carotene corresponds to 0.6 mcg.

Vitamin $B_1$ is very important in red blood cell formation and all of the ingredients of fetal blood cells. Deficiency in the mother can result in acute fetal cardiac failure from significant anemia in the fetus. Since this vitamin is not ubiquitous in a normal diet, the present invention includes about 1 mg/day to about 5 mg/day of Vitamin $B_1$, preferably about 2 mg/per day, as thiamine, to enhance red blood cell formation.

The requirements for Vitamin $B_2$ increase during pregnancy. Deficiency has been associated with fetal malformation of the bony tissue and membranous skeleton, which precedes the cartilageous and osseous skeletons. A deficiency of Vitamin $B_2$ is also linked to hyperemesis gravidarum and an increased incidence of growth restriction and preterm delivery in the fetus. Maternal deficiency of Vitamin $B_2$ is associated with stomatitis, glossitis and cheilosis. The present invention includes about 1 mg/day to about 15 mg/day, preferably about 3.4 mg/day, of Vitamin $B_2$, as riboflavin, to mitigate any deficiency of this vital material during pregnancy.

Vitamin $B_{12}$ is essential for appropriate folic acid metabolism, a deficiency of which is noted by megaloblastic anemia. It also plays a role in maintaining cellular integrity of the central nervous system. Therefore, while supplementation of folic acid may cure hematologic symptoms (anemia) of $B_{12}$ deficiency, it will leave the fetus vulnerable to central nervous system damage. Vitamin $B_{12}$ is found exclusively in animal tissues hence during pregnancy a vegan woman is at risk for $B_{12}$ deficiency. Accordingly, the present invention includes about 2 mcg/day to about 12 mcg/day of Vitamin $B_{12}$, preferably about 2 mcg/day (0.002 mg/day), as cyanocobalamin, to mitigate any deficiency of this essential vitamin.

Vitamin C (ascorbic acid) is essential for the formation of collagen and therefore is very important for both mother and fetus during pregnancy. The transport mechanism across the placenta is the same for that of glucose therefore Vitamin C supplementation is very important in those women having (or at risk for) diabetes. There is a progressive drop in Vitamin C levels during each trimester and if serum levels of this ingredient drop below 80 mg/day habitual abortion, preterm birth and preterm rupture of the membranes may occur. Since there are vagaries of absorption during pregnancy, the present invention includes about 60 mg/day to about 200 mg/day, although possibly as low as 20 mg/day, but preferably about 60 mg/day, of Vitamin C supplementation.

Vitamin $D_3$ (cholecalciferol) regulates calcium homeostasis by maintaining equilibrium (along with parathormone) between calcium resorption and excretion. If Vitamin $D_3$ levels are low, then the mother may lose significant calcium in her urine. If maternal calcium intake is low, then poor bone mineralization is likely to occur in infants. The present invention includes about 200 IU to about 500 IU, preferably about 240 IU (6 mcg)/day, of Vitamin $D_3$ to mitigate these problems in the mother and fetus. Each IU of Vitamin $D_3$ corresponds to 0.025 mcg.

Vitamin E is stored in fat and since the majority of fetal fat deposition occurs after 36 weeks' gestation, the deficiency is very likely to occur in any infant born preterm. Therefore, this is a particularly important ingredient of a prenatal supplement when there is or may be a risk of preterm delivery. Since early births cannot be predicted (occurring from preterm labor as well as medical/surgical complications) the present invention includes about 10 mg/day to about 40 mg/day, preferably about 20 mg/day, of Vitamin E, for example as d-α-tocopherol succinate, regardless of dietary sufficiency. Each IU of d-α-tocopherol succinate corresponds to about 1.12 mg of Vitamin E.

Low levels of lycopene as well as other anti-oxidants are noted to be present in the placenta and fetuses of women with preterm labor, fetal growth restriction, and pre-eclampsia (pregnancy-induced hypertension). Lycopene content is high in tomatoes, but not in other vegetables, thus unless a woman's diet is rich in tomato or tomato-based products there may be a deficiency of this important ingredient. Thus, the present invention includes about 100 mg/day to about 500 mg/day, preferably about 125 mg/day, of a lycopene-containing material for prenatal women at risk for oxidative stress. As commercially available lycopene materials only have about 5% to about 10% lycopene, generally about 5%, the actual lycopene in the supplements of the present invention will be about 5 mg/day to about 25 mg/day of lycopene, preferably about 5 mg/day to about 20 mg/day.

Co-$Q_{10}$ (Co-enzyme $Q_{10}$) is an anti-oxidant that is deficient in the serum of many women with pre-eclampsia. The activity of Co $Q_{10}$ is directed against free radical damage to the endothelial cells lining blood vessels; an abnormality frequently observed in pre-eclampsia. This allows the normal vasodilatation during pregnancy thought to be mediated through nitric oxide. This anti-oxidant works well with Vitamin C in preventing such endothelial damage. Thus, the present invention includes about 50 mg/day to about 200 mg/day, preferably) about 100 mg/day, of Co$Q_{10}$ to enhance the function of Vitamin C and other free radical scavengers.

Omega-3 fatty acids found in marine fats have been shown to be important in the prevention of pre-eclampsia, preterm delivery and early rupture of the membranes. Enhanced, cognitive function and improved visual acuity in babies born to mothers supplemented with docosahexaenoic acid (DHA) have also been noted. Finally, there has been a decrease in maternal postpartum depression when supplemented with DHA. Cold water fish are the highest dietary sources of DHA and it is also available in the eggs of chickens supplemented with micro-algae. Unfortunately, supplementation from these two sources is rare in this country and, therefore, the present invention includes about 50 mg/day to about 250 mg/day, preferably about 100 mg/day, of DHA, which is a beneficial amount for pregnant women.

Due to high levels of progesterone throughout the pregnancy, the small and large intestine become sluggish. Even in the presence of adequate amounts of water, constipation is a tremendous problem in most pregnant women, particularly during the last two trimesters of pregnancy. Iron supplementation (ferrous sulfate and ferrous fumarate) while useful for the mother and developing fetus also increases the chance of constipation and, therefore, the present invention includes about 50 mg/day to about 100 mg/day, preferably about 50 mg/day, of docusate sodium, to help mitigate this annoying, and not to be ignored, problem.

Of all the trace elements, copper has received attention as probably being the most important in human gestation. The metabolism of this element is more altered by pregnancy than any other state. While serum copper rises during pregnancy, due to hormonal changes and protein binding efficiency, levels of copper are low in the fetus; therefore, it is important to supplement this trace element in the diet of pregnant women. Copper is also important as it is associated with a protein in the fetal mitochondria, which disappears shortly after birth. This mitochondrial function is important in most oxidative reactions in rapidly developing fetal tissues. The present inventions includes about 1 mg/day to about 3 mg/day, preferably about 2 mg/day, of copper to ensure that pregnant and nursing women have appropriate levels of copper during these important stages.

Folic acid is probably the most important vitamin during pregnancy. The requirement increases significantly in pregnancy and a deficiency of this vitamin is prevalent among American women. The cardinal result of folic acid deficiency is a maternal anemia that is significantly increased during pregnancy. It has been estimated that 2.5% to 5% of pregnant women in the United States are folic acid-deficient and this is particularly true in indigent patients, adolescents, or those having successive pregnancies with short intervals between them. A deficiency of folic acid results in fetal neural tube defects, preterm delivery, placental abruption and growth restricted fetuses. Since foods in this country are not fortified with folic acid, the present invention includes about 1 mg/day to about 5 mg/day, preferably about 1 mg/day of folic acid.

Because of the blood formation requirements of the fetus and placenta, iron depletion and iron deficiency anemia make this the most common deficiency in pregnancy (90% of all anemias). Heme iron, which is derived from hemoglobin and myoglobin found in meats, is much better absorbed than non-heme, which is found mostly in foods of plant origin (30% versus 5% absorption). People who are vegetarians absorb much less iron than needed during pregnancy. Growth restriction, preterm delivery, and pre-eclampsia have been noted in women who have iron deficiency. One of the problems with iron supplementation is upper GI irritation resulting in nausea, vomiting and a decreased appetite as well as constipation. Thus, the present invention includes about 30 mg/day to about 90 mg/day, preferably about 30 mg/day, of iron, as carbonyl iron that has just under 100% iron content, to mitigate both of these problems. Other pharmaceutically or nutritionally acceptable iron-containing compounds as are known in the art may be used in the supplements of the present invention, for example, ferrous fumarate, ferrous sulfate, etc. The amount of the iron-containing compound used will be the amount that will give about 30 mg/day to about 90 mg/day, preferably about 30 mg/day, of elemental iron content. Thus, for example, if using ferrous fumarate that has about 33% iron content, then about 90 mg/day to about 270 mg/day, preferably about 90 mg/day, of the ferrous fumarate should be used.

Magnesium deficiency has been linked to pre-eclampsia, preterm rupture of the membranes and preterm births secondary to early labor. Women who deliver preterm are more likely to have lower plasma levels of this mineral. The present invention includes about 10/mgday to about 100 mg/day, preferably about 10/mg/day, 20 mg/day or 30 mg/day, of magnesium to supplement any deficiencies that may occur.

Selenium deficiency like iron deficiency and zinc deficiency is common during pregnancy. Low selenium levels have been reported in patients with habitual abortions and in women with pre-eclampsia and cardiomyopathy. Since this mineral is an essential ingredient of the enzyme glutathione peroxidase, it is an important defensive ingredient against free radical damage in blood vessels and the developing fetus. Selenium is a trace element that has the ability to remove hydroperoxides and oxidized lipoproteins. Moreover, selenoprotein is able to scavenge peroxynitrite on the surface of vascular endothelium thus highlighting its role in pre-eclampsia. The present invention includes about 10 mcg/day to about 30 mcg/day, preferably about 15 mcg/day, of selenium to mitigate these problems.

Zinc deficiency produces congenital malformations as well as fetal losses. Since maternal plasma levels of zinc decrease during pregnancy, supplementation is important. In the fetus deficiency of zinc may be involved with premature rupture of the membranes and a reduced ability to fight infection due to suppressed immunity. Zinc deficiency is quite common in the United States, particularly in pregnant women and, therefore, the present invention includes about 15 mg/day to about 30 mg/day, preferably about 25 mg/day, of zinc.

All of the ingredients of the present invention are well known and are commercially available, generally from multiple sources. They may be used in any chemical form known in the art to be suitable for use in nutritional supplements, except that, in certain instances as set forth above, particularly with regard to the preferred and particularly preferred embodiments of the present invention, specific forms are desired, as with beta-carotene for Vitamin A and carbonyl iron for the iron ingredient of the present invention. In addition, the methods of manufacture thereof are well known to those skilled in this art and need not be described further herein.

The compositions of the present invention include any suitable pharmaceutically or nutritionally acceptable carrier as would be known to one skilled in this art. The methods of pharmaceutical formulation applicable to the supplements of the present invention are also well known to one skilled in this art and need not be described further herein. Suitable carriers and methods of formulation are shown, for example, in the Hermelin et al. and Cooper et al. patents cited above and, to the extent necessary, the disclosures thereof pertaining thereto are incorporated herein by this reference. Any dosage form may be utilized as desired, although, given the nature of the ingredients described herein, a conventional tablet, using conventional pharmaceutically or nutritionally acceptable tablet ingredients, is satisfactory and is the preferred form of administration, although other dosage forms, such as caplets or chewable tablets, may be used as well. A single daily tablet taken orally will suffice, generally to be taken at breakfast so as not to be forgotten during the day, although if desired, smaller tablets can be utilized, for example, ones with one-half or one-third the daily dosage to be taken, for example, at other or each mealtimes, or after pregnancy-induced nausea may have subsided. If the daily tablet is considered too large for ease of ingestion, the tablet may be scored so as to be broken in half and taken one after the other or at different times during the day, or chewable tablets may be used. The DHA can also be in its own dosage form (generally a separate tablet or capsule), which can be taken at the same time as the other ingredients or at a different time if so desired. These supplements are particularly suited for being administered to, or to be taken by, pregnant and nursing women and are free of any other added vitamins and minerals. However, they may also be administered to, or to be taken by, women desiring to become pregnant, so that any ensuing pregnancy (and thus the fetus) will be nutritionally supplemented from the very beginning of gestation.

EXAMPLES

Example 1

The following embodiment of the present invention is prepared as an oral tablet to be taken once daily to supplement the nutritional diet of a woman desiring to become pregnant, or a pregnant or nursing woman:

2,500 IU (1.5 mg) of Vitamin A (as beta-carotene),
2 mg of Vitamin $B_1$,
10 mg of Vitamin $B_2$,
2 mcg of Vitamin $B_{12}$,
100 mg of Vitamin C,
240 IU (6 mcg) of Vitamin $D_3$,
20 mg of Vitamin E,
400 mg of a 5% lycopene-containing material (corresponding to about 20 mg of actual lycopene),
100 mg of co-enzyme Q10,
200 mg of docosahexaenoic acid (DHA),
50 mg of docusate sodium,
2 mg of copper,
1 mg of folic acid,
60 mg of iron,
30 mg of magnesium,
15 mcg of selenium,
25 mg of zinc, and
a pharmaceutically or nutritionally acceptable carrier therefor.

Example 2

The following embodiment of the present invention is prepared as an oral tablet to be taken once daily to supplement the nutritional diet of a woman desiring to become pregnant, or a pregnant or nursing woman:

2,500 IU (1.5 mg) of Vitamin A (as beta-carotene),
2 mg of Vitamin $B_1$,
3.4 mg of Vitamin $B_2$,
2 mcg of Vitamin $B_{12}$,
60 mg of Vitamin C,
240 IU (6 mcg) of Vitamin $D_3$,
20 mg of Vitamin E,
125 mg of a 5% lycopene-containing material (corresponding to about 6 mg of actual lycopene),
100 mg of co-enzyme Q10,
100 mg of docosahexaenoic acid (DHA),
50 mg of docusate sodium,
2 mg of copper,
1 mg of folic acid,
30 mg of iron (as carbonyl iron),
20 mg of magnesium,
15 mcg of selenium,
25 mg of zinc, and
a pharmaceutically or nutritionally acceptable carrier therefor.

Example 3

The following embodiment of the present invention is prepared as an oral tablet to be taken once daily to supplement the nutritional diet of a woman desiring to become pregnant, or a pregnant or nursing woman:
- 2,500 IU (1.5 mg) of Vitamin A (as beta-carotene),
- 2 mg of Vitamin $B_1$,
- 3.4 mg of Vitamin $B_2$,
- 2 mcg of Vitamin $B_{12}$,
- 60 mg of Vitamin C,
- 240 IU (6 mcg) of Vitamin $D_3$,
- 20 mg of Vitamin E,
- 200 mg of a 5% lycopene-containing material (corresponding to about 10 mg of actual lycopene),
- 100 mg of co-enzyme Q10,
- 100 mg of docosahexaenoic acid (DHA),
- 50 mg of docusate sodium,
- 2 mg of copper,
- 1 mg of folic acid,
- 30 mg of iron (as carbonyl iron),
- 20 mg of magnesium,
- 15 mcg of selenium,
- 25 mg of zinc, and
- a pharmaceutically or nutritionally acceptable carrier therefor.

Example 4

The following embodiment of the present invention is prepared as an oral dose to be taken daily (as one tablet or split between two tablets) to supplement the nutritional diet of a woman desiring to become pregnant, or a pregnant or nursing woman:
- 2,000 IU (1.2 mg) of Vitamin A (as beta-carotene),
- 2 mg of Vitamin $B_1$,
- 3.4 mg of Vitamin $B_2$,
- 2 mcg of Vitamin $B_{12}$,
- 60 mg of Vitamin C,
- 240 IU (6 mcg) of Vitamin $D_3$,
- 10 mg of Vitamin E,
- 100 mg of a 5% lycopene-containing material (corresponding to about 5 mg of actual lycopene),
- 200 mg of co-enzyme Q10,
- 200 mg of docosahexaenoic acid (DHA),
- 100 mg of docusate sodium,
- 2 mg of copper,
- 1 mg of folic acid,
- 60 mg of iron (as carbonyl iron),
- 10 mg of magnesium,
- 15 mcg of selenium,
- 15 mg of zinc, and
- a pharmaceutically or nutritionally acceptable carrier therefor.

Example 5

The following embodiment of the present invention is prepared as an oral tablet, two of which are to be taken daily to supplement the nutritional diet of a woman desiring to become pregnant, or a pregnant or nursing woman:
- 1,250 IU (0.43 mg) of Vitamin A (Vitamin A acetate),
- 1 mg of Vitamin $B_1$ (as thiamine mononitrate),
- 1.7 mg of Vitamin $B_2$ (as riboflavin),
- 1 mcg of Vitamin $B_{12}$ (as cyanocobalamin),
- 30 mg of Vitamin C,
- 120 IU (3 mcg) of Vitamin $D_3$ (as cholecalciferol),
- 10 IU (11.2 mg) of Vitamin E (as d-alpha tocopheryl succinate),
- 100 mg of a 5% lycopene-containing material (corresponding to about 5 mg of actual lycopene),
- 50 mg of co-enzyme Q10,
- 50 mg of docosahexaenoic acid (DHA),
- 25 mg of docusate sodium,
- 1 mg of copper (as cupric oxide),
- 0.5 mg of folic acid,
- 15 mg of iron (as carbonyl iron/ferrous fumarate),
- 10 mg of magnesium (as magnesium oxide),
- 7.5 mcg of selenium (as sodium selenate),
- 12.5 mg of zinc (as zinc oxide), and
- a pharmaceutically or nutritionally acceptable carrier therefor.

Two of these tablets are to be taken daily, either separately during the day or at the same time, to give the daily dose within the broad embodiment of the present invention as set forth above.

Example 6

The following embodiment of the present invention is prepared as an oral dose to be taken daily (as one tablet or split between two tablets) to supplement the nutritional diet of a woman desiring to become pregnant, or a pregnant or nursing woman:
- 2,500 IU (1.5 mg) of Vitamin A (as beta-carotene),
- 2 mg of Vitamin $B_1$,
- 3.4 mg of Vitamin $B_2$,
- 2 mcg of Vitamin $B_{12}$,
- 60 mg of Vitamin C,
- 240 IU (6 mcg) of Vitamin $D_3$,
- 20 mg of Vitamin E,
- 200 mg of a 5% lycopene-containing material (corresponding to about 10 mg of actual lycopene),
- 100 mg of co-enzyme Q10,
- 200 mg of docosahexaenoic acid (DHA),
- 50 mg of docusate sodium,
- 2 mg of copper,
- 1 mg of folic acid,
- 30 mg of iron (as carbonyl iron),
- 20 mg of magnesium,
- 15 mcg of selenium,
- 25 mg of zinc, and
- a pharmaceutically or nutritionally acceptable carrier therefor.

The embodiments of the present invention can be or are, as shown in the above Examples, substantially free of other added vitamins and minerals.

The tablets of each of the above Examples can be scored to be broken in half for ease of self-administration if desired. This is particularly appropriate with the larger tablet of Example 4. Optionally, the daily dose can be split between two or three tablets to be taken at various times (for example, at meal times) during the day, or chewable tablets may be used.

The supplements of the present invention should be manufactured in accordance with the Current Good Manufacturing Practices in Manufacturing, Packaging, Labeling and Holding Operations for Dietary Supplements as promulgated by the Federal Food and Drug Administration, as the same may be amended from time to time, and other applicable regulations. It has been found that, when providing multiple vitamins in a dietary or nutritional supplement, some degradation of certain of the vitamins may occur over time. Accordingly, the manufacturing specifications for the vitamins should be about 100% to about 175%, preferably about 100% to about 160%, of the dosage amounts set forth above with respect to various embodiments of the present invention. The manufacturing specifications for the other ingredients should be about 100% to 135%, preferably about 100% to about 130%, of the dosage amounts set forth above with respect to various embodiments of the present invention, with the exception of the docusate sodium, where the manufacturing specification should be about 90% to about 110% of the dosage amounts set forth above with respect to various embodiments of the present invention.

Along with the nutritional and other benefits of the supplements of this invention, they may also be helpful in the treatment or management of pre-eclampsia, which occurs with a significant number of pregnant women.

While various embodiments of the present invention have been described, it should be understood that various modifications and adaptations thereof will be apparent to one skilled in this art. Such modifications and adaptations are considered to be within the scope of the present invention, which is limited only by the scope of the following claims.

What is claimed is:

1. A nutritional supplement including folic acid, lycopene and co-enzyme Q10, and a pharmaceutically or nutritionally acceptable carrier therefor, wherein said supplement is free of calcium, chromium, a cyclooxygenase inhibitor, $PGI_2$ mimetic, a thromboxane inhibitor, a compound possessing $PGI_2$ agonistic and thromboxane-inhibiting properties, a compound possessing thromboxane-antagonistic and $PGI_2$-mimetic activities, a thromboxane-antagonist, and a xanthone extract, and wherein said supplement in solid tablet, caplet or capsule form is suitable to be orally administered to, or orally taken by, women desiring to become pregnant, and pregnant and nursing women.

2. The supplement of claim 1 wherein the supplement is additionally free of one or more of potassium, alpha-carotene, choline, lutein, zeaxanthin, and vitamin K.

3. The supplement of claim 1 wherein the supplement is additionally free of one or more of biotin, iodine, and panthothenic acid.

4. The supplement of claim 1 wherein the supplement is additionally free of vitamin $B_3$, and herbs or herb extracts.

5. The supplement of claim 1 wherein the supplement is additionally free of cobalt, iodine, manganese, molybdenum, potassium, sulfur, vitamin $B_3$, vitamin $B_5$, vitamin K, herbs or herb extracts, alpha-carotene, alpha-lipoic acid, biotin, choline, lutein, omega acids other than docosahexaenoic acid, panthothenic acid, succinic acid, and zeaxanthin.

6. The supplement of claim 1 having a daily dose of about 1 mg to about 5 mg of folic acid.

7. The supplement of claim 1 having a daily dose of about 1 mg of folic acid.

8. The supplement of claim 1 having a daily dose of about 5 to about 25 mg of lycopene.

9. The supplement of claim 1 having a daily dose of about 50 to about 200 mg of co-enzyme Q10.

10. The supplement of claim 1 having a daily dose of about 1 mg of folic acid, a daily dose of about 5 to about 25 mg of lycopene, and a daily dose of about 50 to about 200 mg of co-enzyme Q10.

11. The supplement of claim 2 having a daily dose of about 1 mg of folic acid, a daily dose of about 5 to about 25 mg of lycopene, and a daily dose of about 50 to about 200 mg of co-enzyme Q10.

12. The supplement of claim 3 having a daily dose of about 1 mg of folic acid, a daily dose of about 5 to about 25 mg of lycopene, and a daily dose of about 50 to about 200 mg of co-enzyme Q10.

13. The supplement of claim 4 having a daily dose of about 1 mg of folic acid, a daily dose of about 5 to about 25 mg of lycopene, and a daily dose of about 50 to about 200 mg of co-enzyme Q10.

14. The supplement of claim 5 having a daily dose of about 1 mg of folic acid, a daily dose of about 5 to about 25 mg of lycopene, and a daily dose of about 50 to about 200 mg of co-enzyme Q10.

15. The supplement of claim 1 having a daily dose of about 20 mg of lycopene.

16. The supplement of claim 1 having a daily dose of about 10 mg of lycopene.

17. The supplement of claim 1 having a daily dose of about 6 mg of lycopene.

18. The supplement of claim 1 having a daily dose of about 5 mg of lycopene.

19. The supplement of claim 1 wherein the co-enzyme Q10 is present in a daily dose of about 200 mg.

20. The supplement of claim 1 wherein the co-enzyme Q10 is present in a daily dose of about 100 mg.

21. The supplement of claim 1 wherein the co-enzyme Q10 is present in a daily dose of about 50 mg.

22. The supplement of claim 1 wherein the supplement is in the form of a scored tablet that optionally can be broken in half for ease of self-administration by a woman.

23. A method of supplementing the daily nutritional diet of a woman desiring to become pregnant, or a pregnant or nursing woman comprising orally administering to such a woman the supplement of claim 1.

24. A method of supplementing the daily nutritional diet of a woman desiring to become pregnant, or a pregnant or nursing woman comprising orally administering to such a woman once during a twenty-four hour period the supplement of claim 1.

25. A method of supplementing the daily nutritional diet of a woman desiring to become pregnant or a pregnant or nursing woman comprising orally administering to such a woman two or three times during a twenty-four hour period, in the aggregate, the amounts of the ingredients set forth in the supplement of claim 10.

26. A method of supplementing the daily nutritional diet of a woman desiring to become pregnant, or a pregnant or nursing woman comprising orally administering to such a woman the supplement of claim 2.

27. A method of supplementing the daily nutritional diet of a woman desiring to become pregnant, or a pregnant or nursing woman comprising orally administering to such a woman the supplement of claim 3.

28. A method of supplementing the daily nutritional diet of a woman desiring to become pregnant or a pregnant or nursing woman comprising orally administering to such a woman the supplement of claim 4.

29. A method of supplementing the daily nutritional diet of a woman desiring to become pregnant or a pregnant or nursing woman comprising orally administering to such a woman the supplement of claim 5.

30. A method of supplementing the daily nutritional diet of a woman desiring to become pregnant or a pregnant or nursing woman comprising orally administering to such a woman the supplement of claim 10.

31. A method of supplementing the daily nutritional diet of a woman desiring to become pregnant or a pregnant or nursing woman comprising orally administering to such a woman the supplement of claim 11.

32. A method of supplementing the daily nutritional diet of a woman desiring to become pregnant or a pregnant or nursing woman comprising orally administering to such a woman the supplement of claim 12.

33. A method of supplementing the daily nutritional diet of a woman desiring to become pregnant or a pregnant or nursing woman comprising orally administering to such a woman the supplement of claim 13.

34. A method of supplementing the daily nutritional diet of a woman desiring to become pregnant or a pregnant or nursing woman comprising orally administering to such a woman the supplement of claim 14.

35. A nutritional supplement including folic acid, lycopene, co-enzyme Q10, docosahexaenoic acid, and a pharmaceutically or nutritionally acceptable carrier therefor, wherein said supplement is free of calcium, chromium, a cyclooxygenase inhibitor, $PGI_2$ mimetic, a thromboxane inhibitor, a compound possessing $PGI_2$ agonistic and thromboxane-inhibiting properties, a compound possessing thromboxane-antagonistic and $PGI_2$-mimetic activities, a thromboxane-antagonist, and a xanthone extract, and wherein said supplement in solid tablet, caplet or capsule form is suitable to be orally administered to, or orally taken by, women desiring to become pregnant, and pregnant and nursing women.

36. The supplement of claim 35 wherein the supplement is additionally free of one or more of potassium, alpha-carotene, choline, lutein, zeaxanthin, and vitamin K.

37. The supplement of claim 35 wherein the supplement is additionally free of one or more of biotin, iodine, and panthothenic acid.

38. The supplement of claim 35 wherein the supplement is additionally free of vitamin $B_3$, and herbs or herb extracts.

39. The supplement of claim 35 wherein the supplement is additionally free of cobalt, iodine, manganese, molybdenum, potassium, sulfur, vitamin $B_3$, vitamin $B_5$, vitamin K, herbs or herb extracts, alpha-carotene, alpha-lipoic acid, biotin, choline, lutein, omega acids other than docosahexaenoic acid, panthothenic acid, succinic acid, and zeaxanthin.

40. The supplement of claim 35 having a daily dose of about 1 mg to about 5 mg of folic acid.

41. The supplement of claim 35 having a daily dose of about 1 mg of folic acid.

42. The supplement of claim 35 having a daily dose of about 5 to about 25 mg of lycopene.

43. The supplement of claim 35 having a daily dose of about 50 to about 200 mg of co-enzyme Q10.

44. The supplement of claim 35 having a daily dose of about 50 to about 250 mg of docosahexaenoic acid.

45. The supplement of claim 35 having a daily dose of about 1 mg of folic acid, a daily dose of about 5 to about 25 mg of lycopene, a daily dose of about 50 to about 200 mg of co-enzyme Q10, and a daily dose of about 50 to about 250 mg of docosahexaenoic acid.

46. The supplement of claim 35 having a daily dose of about 5 mg of lycopene.

47. The supplement of claim 35 having a daily dose of about 6 mg of lycopene.

48. The supplement of claim 35 having a daily dose of about 10 mg of lycopene.

49. The supplement of claim 35 having a daily dose of about 20 mg of lycopene.

50. The supplement of claim 35 having a daily dose of about 100 mg of co-enzyme Q10.

51. The supplement of claim 35 having a daily dose of about 200 mg of co-enzyme Q10.

52. The supplement of claim 35 having a daily dose of about 100 mg of docosahexaenoic acid.

53. The supplement of claim 35 having a daily dose of about 200 mg of docosahexaenoic acid.

54. The supplement of claim 35 having a daily dose of about 1 mg of folic acid, a daily dose of about 10 mg of lycopene, a daily dose of about 100 mg of co-enzyme Q10, and a daily dose of about 100 mg of docosahexaenoic acid.

55. The supplement of claim 35 having a daily dose of about 1 mg of folic acid, a daily dose of about 5 mg of lycopene, a daily dose of about 200 mg of co-enzyme Q10, and a daily dose of about 200 mg of docosahexaenoic acid.

56. A method of supplementing the daily nutritional diet of a woman desiring to become pregnant, or a pregnant or nursing woman comprising orally administering to such a woman the supplement of claim 35.

57. A method of supplementing the daily nutritional diet of a woman desiring to become pregnant or a pregnant or nursing woman comprising orally administering to such a woman the supplement of claim 45.

* * * * *